United States Patent
Ariyoshi et al.

(10) Patent No.: US 8,937,652 B2
(45) Date of Patent: Jan. 20, 2015

(54) ENDOSCOPE APPARATUS AND DETERIORATION DETECTION METHOD OF POLARIZATION ELEMENT OF ENDOSCOPE

(71) Applicant: Olympus Medical Systems Corp., Tokyo (JP)

(72) Inventors: Daiki Ariyoshi, Hino (JP); Kazuhiro Gono, Sagamihara (JP); Kenji Yamazaki, Hino (JP); Ryo Machida, Kanagawa (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/210,763

(22) Filed: Mar. 14, 2014

(65) Prior Publication Data

US 2014/0204188 A1 Jul. 24, 2014

Related U.S. Application Data

(63) Continuation of application No. PCT/JP2013/076898, filed on Oct. 3, 2013.

(30) Foreign Application Priority Data

Oct. 9, 2012 (JP) ................. 2012-224408

(51) Int. Cl.
*H04N 7/18* (2006.01)
*A61B 1/04* (2006.01)
*H04N 5/225* (2006.01)
*A61B 1/00* (2006.01)
*G02B 23/24* (2006.01)
*H04N 17/02* (2006.01)
*G02B 23/26* (2006.01)

(52) U.S. Cl.
CPC ............. *H04N 5/2256* (2013.01); *A61B 1/00* (2013.01); *A61B 1/04* (2013.01); *G02B 23/2407* (2013.01); *A61B 1/00057* (2013.01); *H04N 17/02* (2013.01); *G02B 23/26* (2013.01)
USPC ........................................................ 348/68

(58) Field of Classification Search
CPC ....... H04N 5/2256; H04N 17/02; A61B 1/00; A61B 1/04; A61B 1/00057; G02B 23/2407; G02B 23/26
USPC ............................................. 348/65, 68, 675
See application file for complete search history.

(56) References Cited

U.S. PATENT DOCUMENTS 5,565,931 A * 10/1996 Girod ............................ 348/675

FOREIGN PATENT DOCUMENTS

| JP | 2588460 B2 | 3/1997 |
|---|---|---|
| JP | 2007-143580 A | 6/2007 |
| JP | 2008-008777 A | 1/2008 |

OTHER PUBLICATIONS

English Abstract of JP 05-307144, dated Nov. 19, 1993.

*Primary Examiner* — Allen Wong
(74) *Attorney, Agent, or Firm* — Scully, Scott, Murphy & Presser, P.C.

(57) ABSTRACT

An endoscope apparatus includes a flash memory that stores a reference value of a color balance adjustment value of an endoscopic image of an endoscope that picks up an object through a polarizer. The endoscope calculates, from the reference value and the color balance adjustment value of the endoscope after elapse of a predetermined time period, an amount of change in the color balance adjustment value; judges whether or not the calculated amount of change is equal to or larger than a predetermined threshold; and, when the amount of change is equal to or larger than the predetermined threshold, outputs a predetermined output.

15 Claims, 12 Drawing Sheets

| SCOPE ID |
|---|
| ACCUMULATED TIME PERIOD OF USE Ta |
| REFERENCE COLOR BALANCE ADJUSTMENT VALUE Rg |
| POLARIZER DETERIORATION INFORMATION F |

FIG.14

| SCOPE ID |
|---|
| ACCUMULATED TIME PERIOD OF USE Ta |
| REFERENCE COLOR BALANCE ADJUSTMENT VALUE Rg1 FOR LIGHT SOURCE APPARATUS 4-1 |
| REFERENCE COLOR BALANCE ADJUSTMENT VALUE Rg2 FOR LIGHT SOURCE APPARATUS 4-2 |
| REFERENCE COLOR BALANCE ADJUSTMENT VALUE Rg3 FOR LIGHT SOURCE APPARATUS 4-3 |
| ⋮ |
| POLARIZER DETERIORATION INFORMATION F |

ENDOSCOPE APPARATUS AND DETERIORATION DETECTION METHOD OF POLARIZATION ELEMENT OF ENDOSCOPE

CROSS REFERENCE TO RELATED APPLICATION

This application is a continuation application of PCT/JP2013/076898 filed on Oct. 3, 2013 and claims benefit of Japanese Application No. 2012-224408 filed in Japan on Oct. 9, 2012, the entire contents of which are incorporated herein by this reference.

BACKGROUND OF THE INVENTION

1. Field of the Invention

The present invention relates to an endoscope apparatus and a method for detecting deterioration of a polarizer of an endoscope.

2. Description of the Related Art

Conventionally, endoscopes have been widely used in medical and industrial fields. For example, in the medical field, a surgeon can conduct examination of the inside of a subject by inserting an insertion portion of an endoscope into the subject and displaying an image of the inside of the subject picked up by an image pickup section provided at a distal end portion of the insertion portion on a monitor.

The distal end portion of the insertion portion of the endoscope is provided with an illumination window and an observation window. An illumination light is emitted from the illumination window to illuminate the subject, and a light reflected from the subject is received by an image pickup device through the observation window.

A polarizer is provided for each of an illumination optical system provided for the illumination window of the endoscope and an observation optical system provided for the observation window. For example, by causing polarization directions of the two polarizers to be the same, only a light from a mucosal surface of the subject is received by the image pickup device so that a surface structure of a mucosa can be easily seen. It is also possible to prevent halation by causing the polarization directions of the two polarizers to cross at right angles, as disclosed in Japanese Patent No. 2588460 and Japanese Patent Application Laid-Open Publication No. 2007-143580.

SUMMARY OF THE INVENTION

An endoscope apparatus of an aspect of the present invention includes: a storage section that stores a reference value, which is a color balance adjustment value at a time of adjusting an endoscopic image obtained from an endoscope to be of predetermined color balance, in the endoscope that picks up an object through a polarizer; an amount-of-change calculating section that calculates, from the reference value stored in the storage section and the color balance adjustment value at the time of adjusting the endoscopic image after elapse of a predetermined time period to be of the predetermined color balance, an amount of change in the color balance adjustment value; a judgment section that judges whether or not the amount of change calculated at the amount-of-change calculating section is equal to or larger than a predetermined threshold; and an output section that performs a predetermined output when it is judged at the judgment section that the amount of change is equal to or larger than the predetermined threshold.

A method for detecting deterioration of a polarizer of an endoscope of an aspect of the present invention includes: storing a reference value, which is a color balance adjustment value at a time of adjusting an endoscopic image obtained from an endoscope to be of predetermined color balance, in the endoscope that picks up an object through the polarizer, into a storage section; calculating, from the reference value stored in the storage section and the color balance adjustment value at the time of adjusting the endoscopic image after elapse of a predetermined time period to be of the predetermined color balance, an amount of change in the color balance adjustment value; judging whether or not the calculated amount of change is equal to or larger than a predetermined threshold; and performing a predetermined output when it is judged that the amount of change is equal to or larger than the predetermined threshold.

An endoscope apparatus of an aspect of the present invention includes: a storage section that stores a reference value of a light adjustment value of a light source apparatus connected to an endoscope that picks up an object through a polarizer; an amount-of-change calculating section that calculates, from the reference value stored in the storage section and the light adjustment value of the light source apparatus after elapse of a predetermined time period, an amount of change in the light adjustment value of the light source apparatus; a judgment section that judges whether or not the amount of change calculated at the amount-of-change calculating section is equal to or larger than a predetermined threshold; and an output section that performs a predetermined output when it is judged at the judgment section that the amount of change is equal to or larger than the predetermined threshold.

A method for detecting deterioration of a polarizer of an endoscope of an aspect of the present invention includes: storing a reference value of a light adjustment value of a light source apparatus connected to an endoscope that picks up an object through the polarizer, into a storage section; calculating, from the reference value stored in the storage section and the light adjustment value of the light source apparatus after elapse of a predetermined time period, an amount of change in the light adjustment value of the light source apparatus; judging whether or not the calculated amount of change is equal to or larger than a predetermined threshold; and performing a predetermined output when it is judged that the amount of change is equal to or larger than the predetermined threshold.

BRIEF DESCRIPTION OF THE DRAWINGS

FIG. 14 is a diagram showing an example of information stored in a flash memory 19 of an endoscope 2 according to a variation 1 of the first and second embodiments of the present invention.

DETAILED DESCRIPTION OF THE PREFERRED EMBODIMENTS

Embodiments of the present invention will be described below with reference to drawings.

First Embodiment

Figure 1:
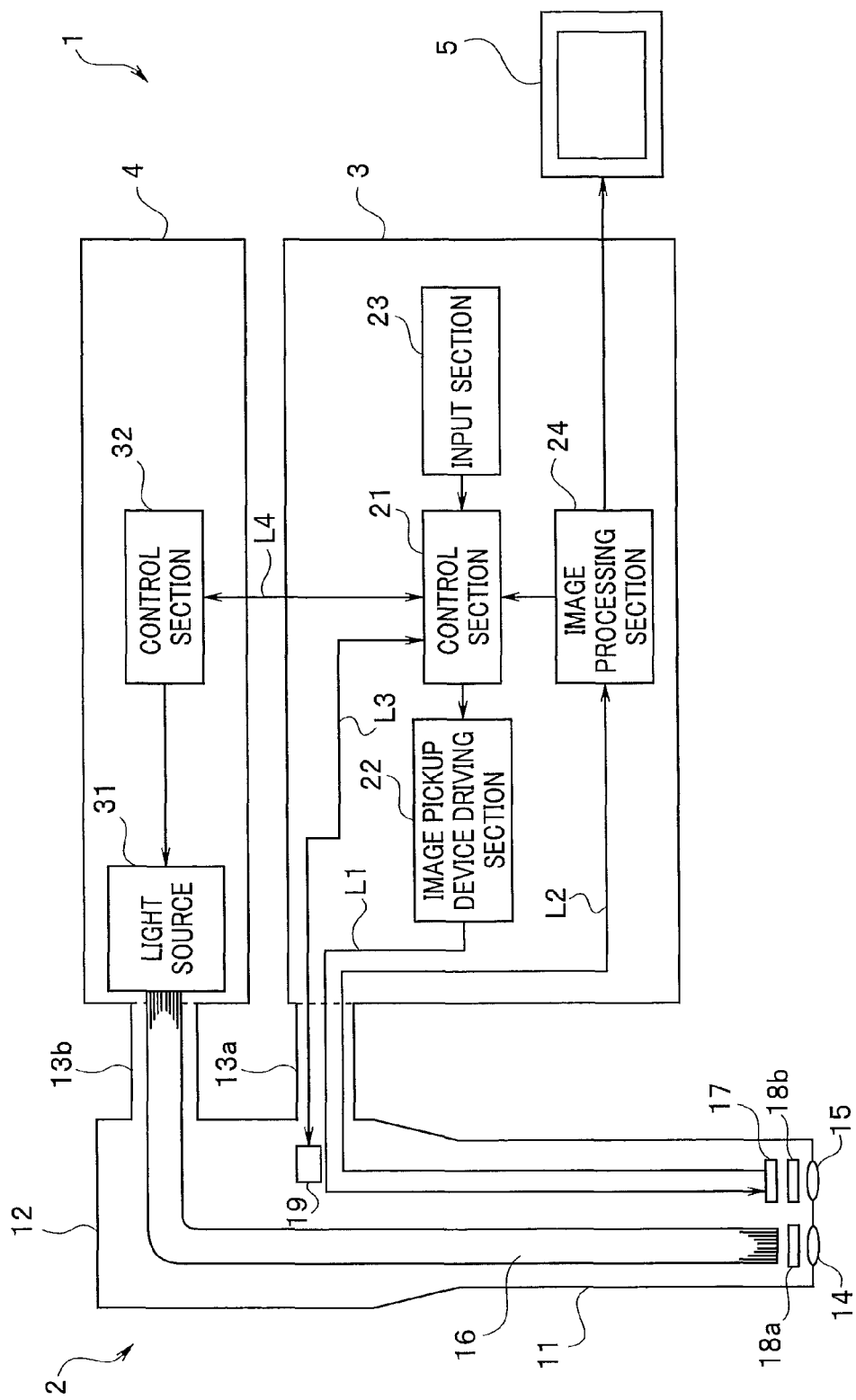
FIG. 1 is a configuration diagram showing a schematic configuration of an endoscope apparatus according to a first embodiment of the present invention.

FIG. 1 is a configuration diagram showing a schematic configuration of an endoscope apparatus according to a first embodiment of the present invention. An endoscope apparatus 1 is configured with an endoscope 2, a body device 3, a light source apparatus 4 and a display device 5. The endoscope 2 is configured with an elongated insertion portion 11, an operation section 12 to which a proximal end of the insertion portion 11 is connected, two connection cables 13a and 13b extending from a side part of the operation section 12. A connector not shown is provided at an end part of each of the connection cables 13a and 13b of the endoscope 2. The endoscope 2 and the body device 3 are connected by the connection cable 13a, and the endoscope 2 and the light source apparatus 4 are connected by the connection cable 13b. The display device 5 is connected to the body device 3.

A distal end portion of the insertion portion 11 of the endoscope 2 is provided with an illumination optical system 14 provided for the illumination window and an objective optical system 15 provided for the observation window. On a back side of the illumination optical system 14, a distal end face of a light guide 16 which guides an illumination light and emits the illumination light from a distal end is arranged. On a back side of the objective optical system 15, an image pickup device 17 is arranged.

Furthermore, between the illumination optical system 14 and the distal end face of the light guide 16, a polarizer 18a is arranged. Between the objective optical system 15 and an image pickup surface of the image pickup device 17, a polarizer 18b is arranged. Here, the polarizers 18a and 18b are wire grid type polarizers, the transmittance of which is higher than that of an absorption type polarizer. Note that the polarizers 18a and 18b may be absorption type polarizers.

The two polarizers 18a and 18b are provided at the distal end portion of the insertion portion 11, with a rotation angle around an optical axis adjusted so that their polarization directions are a same direction. Here, a structure of a mucosal surface of a subject becomes easy to see by causing a polarization direction of an illumination light emitted from the illumination window and a polarization direction of a reflected light which enters from the observation window to be the same. That is, the endoscope 2 picks up an image of an object through the polarizers 18a and 18b.

Furthermore, the endoscope 2 includes a flash memory 19 which is a rewritable nonvolatile memory.

The body device 3 is configured including a control section 21, an image pickup device driving section 22, an input section 23 and an image processing section 24.

The control section 21 is connected to each of the sections (the image pickup device driving section 22, the input section 23 and the image processing section 24) and the light source apparatus 4 in the endoscope apparatus 1 to control each of the sections and the light source apparatus 4 so that various functions of the endoscope apparatus 1 are realized. A configuration of the control section 21 will be described later.

The light source apparatus 4 has a light source 31 which includes multiple light emitting diodes (hereinafter referred to as LEDs) and a control section 32, and the control section 32 controls the light source 31 to light up and generate an illumination light, under control of the control section 21 of the body device 3. The multiple LEDs of the light source 31 include LEDs in three colors of RGB, and output of each color can be adjusted. Note that light-emitting devices used as the light source may be lasers instead of LEDs.

In the state that the endoscope 2 and the light source apparatus 4 are connected by the connection cable 13b, a proximal end surface of the light guide 16 is positioned at an emission section of the light source 31. A light from the light source 31 is led into the light guide 16 from the proximal end surface of the light guide 16 and emitted from a distal end surface of the light guide 16 as an illumination light.

When the endoscope 2 and the body device 3 are connected by the connection cable 13a, the image pickup device 17 in the endoscope 2 is connected to the image pickup device driving section 22 and the image processing section 24 by signal lines L1 and L2, and the flash memory 19 and the control section 21 are connected by a signal line L3.

The image pickup device driving section 22 is a circuit which generates a drive signal for driving the image pickup device 17 of the endoscope 2 and outputs the drive signal to the image pickup device 17 via the signal line L1.

The input section 23 includes various switches, including a power switch for turning on/off the body device 3, a keyboard and the like, so that various commands can be inputted by a user.

The image processing section 24 receives an image pickup signal from the image pickup device 17 via the signal line L2, converts the image pickup signal to a digital signal, executes various correction processes, and outputs a video signal for displaying an endoscopic image to the display device 5.

Furthermore, the control section 21 is connected to the flash memory 19 of the endoscope 2 via the signal line L3 so that it is possible to write data to the flash memory 19 and read data from the flash memory 19.

The control section 21 of the body device 3 and the control section 32 of the light source apparatus 4 are connected via a communication line L4 of a connection cable (not shown) so that the control section 21 and the control section 32 can mutually communicate with each other.

Note that, though the body device 3 and the light source apparatus 4 are separate apparatuses in FIG. 1, the light source apparatus 4 and the body device 3 may be configured as an integrated apparatus.

Figure 2:
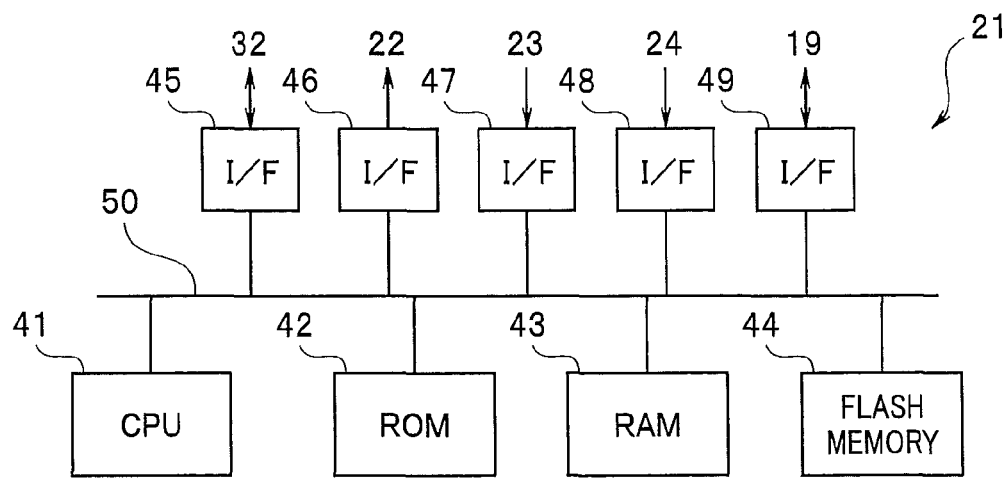
FIG. 2 is a block diagram showing a configuration of a control section 21 according to the first embodiment of the present invention.

FIG. 2 is a block diagram showing a configuration of the control section 21. The control section 21 includes a central processing unit (hereinafter referred to as a CPU) 41, a ROM 42, a RAM 43, a flash memory 44 which is a nonvolatile memory, and various interfaces (hereinafter abbreviated as I/Fs) 45, 46, 47, 48 and 49. The CPU 41, the ROM 42, the RAM 43, the flash memory 44 and the various interfaces (hereinafter abbreviated as I/Fs) 45, 46, 47, 48 and 49 are connected to one another by a bus 50.

The CPU 41 reads a program stored in the ROM 42 and executes the program using the RAM 43 as a working area. Programs stored in the ROM 42 include a program for detecting deterioration of polarizers to be described later, and the like. The CPU 41 can perform writing and reading of data to and from the flash memory 44 when executing a program.

The I/F 45 is an interface with the control section 32 of the light source apparatus 4. The I/F 46 is an interface with the image pickup device driving section 22. The I/F 47 is an interface with the input section 23. The I/F 48 is an interface with the image processing section 24. The I/F 49 is an interface with the flash memory 19 of the endoscope 2.

For example, when the user inputs a command for displaying an endoscopic image on the display device 5 to the input section 23, the CPU 41 receives the command from the user, from the input section 23 via the I/F 47. In response to the instruction command, the CPU 41 reads and executes a predetermined program from the ROM 42 to drive the image pickup device driving section 22 and control the image processing section 24 to display an image signal of the endoscopic image on the display device 5.

Figure 3A:
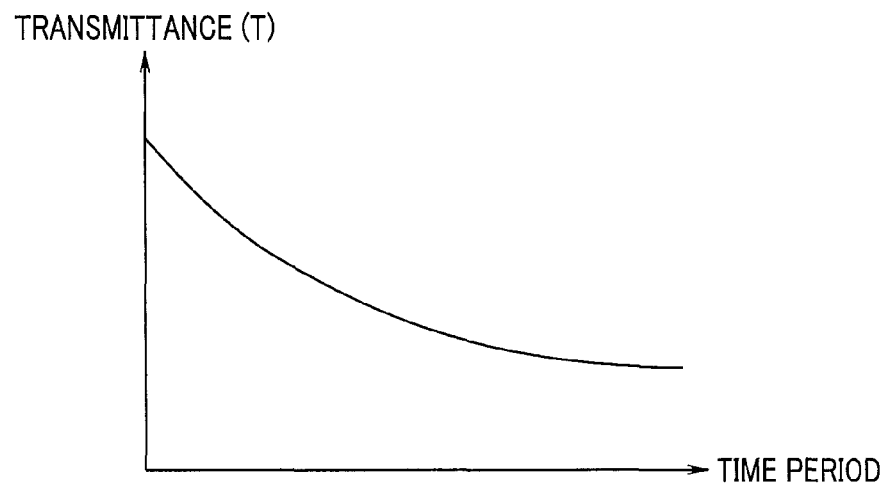
FIG. 3A is a diagram for illustrating an example of a transmittance characteristic of each of polarizers 18a and 18b according to elapse of a time period, according to the first embodiment of the present invention.
Figure 3B:
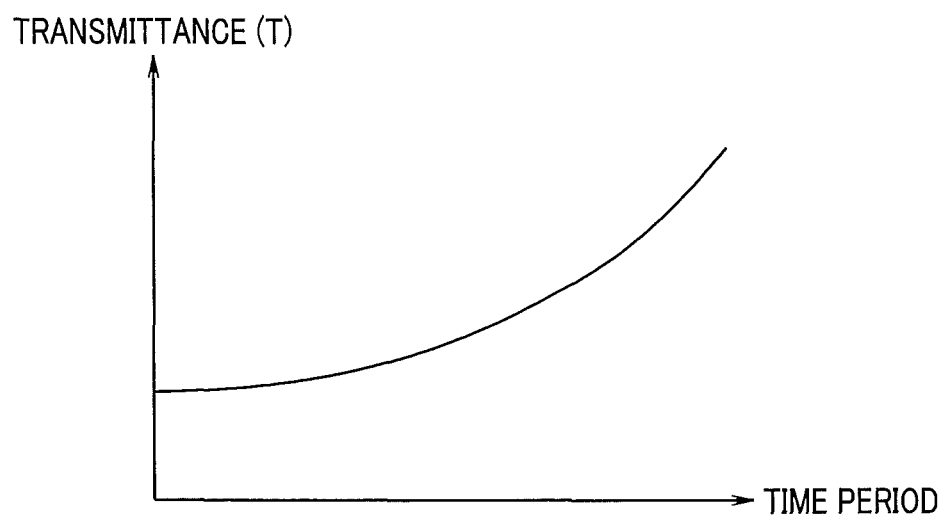
FIG. 3B is a diagram showing an example of a transmittance characteristic of another polarizer.

Here, a transmittance characteristic of a polarizer will be described. FIG. 3A is a diagram for illustrating an example of a transmittance characteristic of each of polarizers 18a and 18b according to elapse of a time period. FIG. 3B is a diagram showing a transmittance characteristic of another polarizer. The transmittance characteristic differs according to polarizer. For example, in FIG. 3A, the transmittance of the polarizer decreases with elapse of a time period. In FIG. 3B, the transmittance of the polarizer increases with elapse of a time period.

The polarizers 18a and 18b are wire grid type polarizers as described above. In the case of wire grid type polarizers, the polarizers have different transmittance characteristics within a visible light wavelength range, for example, within a range of 400 nm to 700 nm. Furthermore, transmittance T of each color changes with elapse of a time period as shown in FIGS. 3A and 3B. This is because the polarizers 18a and 18b deteriorate due to elapse of a time period and due to heat.

When the polarizers deteriorate, an effect of polarization decreases. For example, an extinction ratio (a ratio of a light transmission amount in a state that polarization directions of the two polarizers are in parallel to each other to a light transmission amount in a crossed Nichol prism state that the polarization directions of the two polarizers cross at right angles) decreases. The deterioration of the polarizers gradually progresses, it is difficult for a surgeon to know the deterioration of the polarizers only by looking at endoscopic images.

Therefore, as described later, the control section 21 of the endoscope apparatus 1 of the present embodiment detects deterioration of the polarizers 18a and 18b. When deterioration is detected, the control section 21 performs a predetermined output, for example, a message display or the like to prompt the user, such as a surgeon, to repair the endoscope to replace the polarizers 18a and 18b.

Figures 4, 5:
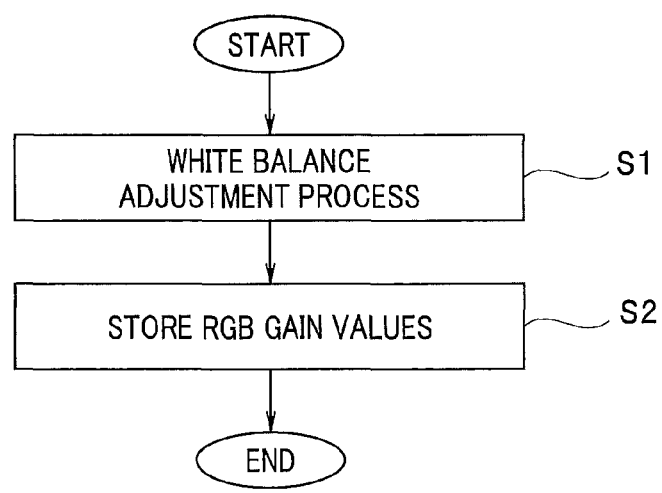
FIG. 4 is a diagram showing an example of information stored in a flash memory 19 of an endoscope 2 according to the first embodiment of the present invention.
FIG. 5 is a flowchart showing an example of a flow of a procedure for setting a reference color balance adjustment value Rg, according to the first embodiment of the present invention.

FIG. 4 is a diagram showing an example of information stored in the flash memory 19 of the endoscope 2. The flash memory 19 includes a storage area for storing a scope ID, which is an identification code of the endoscope 2, an accumulated time period of use Ta, a reference color balance adjustment value Rg and polarizer deterioration information F. Data of the flash memory 19 can be read and written by the CPU 41 via the signal line L3.

The scope ID is an identifier specific to the endoscope 2. The scope ID is determined when the endoscope 2 is manufactured and is stored in the flash memory 19. When the endoscope 2 is manufactured, the accumulated time period of use Ta is set to 0 (zero) and stored into the flash memory 19.

The accumulated time period of use Ta is an accumulated time period during which the endoscope 2 is connected to the body device 3 and used, and is written by the body device 3 when the endoscope 2 is used.

More specifically, when detecting that the endoscope 2 is connected to the body device 3, the CPU 41 of the control section 21 assumes that the endoscope 2 is energized and updates the accumulated time period of use Ta in the flash memory 19 at predetermined time periods during energization. For example, the CPU 41 updates the accumulated time period of use Ta by incrementing data of the accumulated time period of use Ta every one minute.

Note that, though summing up of the accumulated time period of use Ta is performed by the CPU 41 of the body device 3, the data of the accumulated time period of use Ta may be updated by a circuit or the like provided for the endoscope 2.

Furthermore, note that, though an accumulated time period of time periods of energization to the endoscope 2 is regarded as the accumulated time period of use Ta of the endoscope 2 on the assumption that the endoscope 2 is used while it is energized, time period information about other states may be used as the accumulated time period of use Ta of the endoscope 2. For example, a time period during which the CPU 41 outputs a light-up instruction to the light source apparatus 4 may be counted and set as the accumulated time period of use Ta of the endoscope 2.

Furthermore, note that the accumulated time period of use Ta may be stored in the flash memory 44 of the body device 3.

The accumulated time period of use Ta cannot be rewritten until the polarizers 18a and 18b are replaced because of repair or the like of the endoscope 2.

The reference color balance adjustment value Rg is reference information to be a criterion for judging deterioration of the polarizers 18a and 18b to be described later. Here, the reference color balance adjustment value Rg is a gain value for each of RGB color signals, which is obtained by a white balance process performed at the time of manufacturing an endoscope the polarizers 18a and 18b of which have not deteriorated. That is, the flash memory 19, which is a storage section, stores a reference value of the color balance adjustment value for an endoscopic image of the endoscope 2.

Note that, though the accumulated time period of use Ta of the endoscope 2 is stored in the flash memory 19 of the endoscope 2 here, the accumulated time period of use Ta may be stored in the flash memory 44 of the body device 3.

Here, a procedure for setting the reference color balance adjustment value Rg will be described. FIG. 5 is a flowchart showing an example of a flow of a procedure for setting the reference color balance adjustment value Rg. The process in FIG. 5 is executed by an examination apparatus involved in endoscope manufacture.

As shown in FIG. 5, in a factory, a white balance adjustment process is executed for manufactured endoscopes (S1). The endoscope 2 is connected to the light source apparatus 4 used in combination with the endoscope 2 or a light source apparatus which emits a white light to be a criterion, and the white balance adjustment process is executed.

The white balance adjustment process is performed, for example, in a state that the distal end portion of the insertion portion 11 of the endoscope 2 is covered with a predetermined cap for white balance with its internal surface painted with white paint. In the white balance adjustment process, a white image is picked up, and gain adjustment is performed for each of RGB color signals so that the strengths of the three RGB color signals become the same.

The obtained gain value of each of the RGB color signals is stored into the flash memory 19 of the endoscope 2 as the reference color balance adjustment value Rg as the reference information for judging deterioration of the polarizers 18a and 18b to be described later (S2).

As described above, the white balance process is performed for the manufactured endoscope 2 in the factory, and the gain value of each color signal, which is a color balance adjustment value at the time when the polarizers 18a and 18b of the endoscope 2 have not deteriorated, is stored into the flash memory 19 as the reference color balance adjustment value Rg. That is, the color balance adjustment value is the gain value of each color at the time when the white balance adjustment is performed for an endoscopic image.

After that, the reference color balance adjustment value Rg is not rewritten until the endoscope 2 is repaired and the white balance process is performed again in the factory.

Note that, though the gain value of each color obtained when white balance adjustment is performed at the time of manufacturing the endoscope 2 is written into the flash memory 19 here, a gain value obtained when the endoscope 2 is used in a hospital or the like for the first time and white balance adjustment is performed is also possible. For example, when a value is not stored even if the CPU 41 reads the reference color balance adjustment value Rg in the flash memory 19 of the endoscope 2, white balance adjustment is performed in a hospital or the like. Therefore, the control section 21 of the body device 3 writes the gain value of each color signal obtained then into the flash memory 19 as the reference color balance adjustment value Rg.

The polarizer deterioration information F is information indicating that deterioration of the polarizers 18a and 18b has been judged. When the endoscope 2 is manufactured, the polarizer deterioration information F, which is flag information, is set to "0 (zero)" and stored into the flash memory 19.

The polarizer deterioration information F cannot be rewritten until the endoscope 2 is repaired and the polarizers 18a and 18b are replaced in the factory.

As described above, when the endoscope 2 is manufactured, the scope ID, the accumulated time period of use Ta, the reference color balance adjustment value Rg and the polarizer deterioration information F are stored into the flash memory 19 of the endoscope 2. Then, in a hospital, the endoscope 2 is connected to the body device 3 and the light source apparatus 4 and used for an endoscopy.

As described above, since the polarizers 18a and 18b of the endoscope 2 deteriorate with elapse of a time period and with heat, a process for detecting deterioration of the polarizers 18a and 18b of the endoscope 2 is performed in the endoscope apparatus 1.

Figure 6:
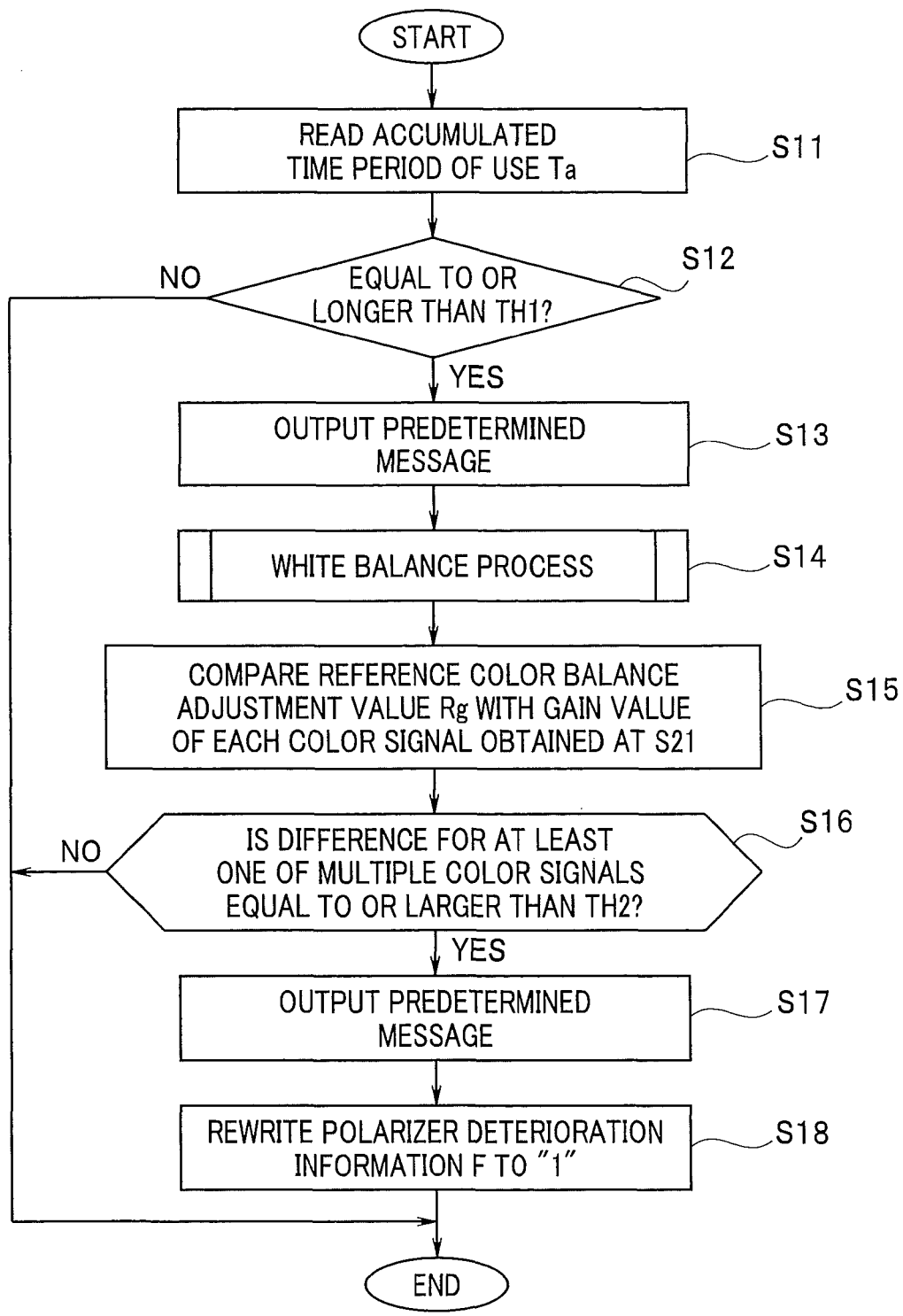
FIG. 6 is a flowchart showing an example of a flow of a process for detecting deterioration of the polarizers of the endoscope 2 according to the first embodiment of the present invention.

FIG. 6 is a flowchart showing an example of a flow of the process for detecting deterioration of the polarizers of the endoscope 2. The process in FIG. 6 is performed by the CPU 41 of the control section 21 reading and executing a program for the process for detecting deterioration of the polarizers of the endoscope 2 in FIG. 6 when the endoscope 2 is connected to the body device 3 and power is turned on.

First, the CPU 41 reads information about the accumulated time period of use Ta of the endoscope 2 from the flash memory 19 (S11).

Next, the CPU 41 judges whether or not the read accumulated time period of use Ta is equal to or longer than a predetermined time period TH1 (S12). The predetermined time period TH1 is, for example, several hours or dozens of hours, and it is a threshold of an elapsed time period after time of starting use of the endoscope for judging deterioration of the polarizers 18a and 18b. That is, the predetermined time period TH1 is a time period set to judge deterioration of the polarizers 18a and 18b of the endoscope 2.

As described above, when the accumulated time period of use Ta of the endoscope is equal to or longer than the predetermined time period (TH1), calculation of an amount of change in the color balance adjustment value and judgment about whether or not the amount of change is equal to or larger than a predetermined threshold, which are to be described later, are performed.

When the accumulated time period of use Ta which has been read is neither equal to nor longer than the predetermined time period TH1 (S12: NO), the process ends without doing anything.

When the read accumulated time period of use Ta is equal to or longer than the predetermined time period TH1, the CPU 41 outputs a predetermined message to the display device 5 (S13). The predetermined message is, for example, a message saying "Perform a white balance process."

In response to the message, the white balance process is executed by the user.

Figure 7:
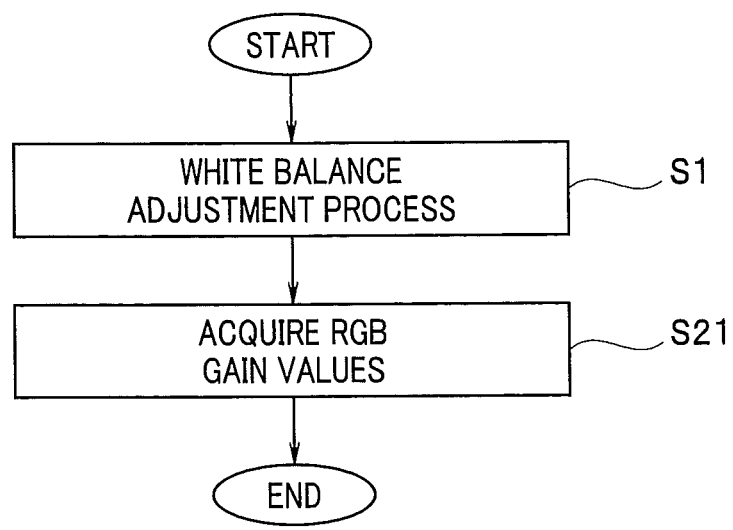
FIG. 7 is a flowchart showing an example of a flow of a white balance process (S14) in FIG. 6.

The white balance process is a process similar to the above-described process shown in FIG. 5. FIG. 7 is a flowchart showing an example of a flow of the white balance process (S14) in FIG. 6. The CPU 41 executes a white balance adjustment process which is a same process as step 51 in FIG. 5 (S1). In the white balance adjustment process, the user is prompted to cover the distal end portion of the insertion portion 2 with a predetermined white balance cap to perform white balance adjustment, and image pickup by the image pickup device 17 is performed in the state that the distal end portion of the insertion portion 2 is covered with the predetermined white balance cap. In the white balance adjustment process, gain adjustment for each of RGB color signals is performed for an obtained image, and the CPU 41 acquires a gain value of each of the RGB color signals (S21).

Returning to FIG. 6, the CPU 41 compares the reference color balance adjustment value Rg with the RGB gain values acquired at S14 (S22) (S15). That is, comparison between the gain value of each of the RGB color signals acquired at S21 and a gain value of each of the RGB color signals included in the reference color balance adjustment value Rg is performed. Thus, the process of S15 constitutes an amount-of-change calculating section which calculates an amount of change in the color balance adjustment value from the reference color balance adjustment value Rg, which is a reference value, and the color balance adjustment value of the endoscope 2 after elapse of the predetermined time period (TH1).

More specifically, an absolute value of difference between the gain value of each color signal obtained at S21 and the gain value of each color signal included in the reference color balance adjustment value Rg is determined for each of the RGB color signals, and the absolute value of the difference between the gain values is calculated for each of the three RGB color signals.

The CPU 41 judges whether or not at least one of the absolute values of the three differences for the RGB gain values is equal to a predetermined threshold TH2 (S16). That is, the process of S16 constitutes a judgment section which judges whether or not the calculated amount of change in the color balance adjustment value is equal to or larger than the predetermined threshold (TH2).

If any one of the three absolute values of difference is equal to or larger than the predetermined threshold TH2 (S16: YES), the CPU 41 outputs a predetermined message to the display device 5 (S17). The predetermined message of S17 is, for example, a message saying "Request repair of the endoscope 2." That is, the process of S17 constitutes an output section which performs a predetermined output when the amount of change in the color balance adjustment value is equal to or larger than the predetermined threshold (TH2). As described above, at S17, a predetermined output is performed when at least one of color signals of respective colors of an endoscopic image is equal to or larger than the predetermined threshold (TH2).

At S17, the predetermined output is a message output for displaying a predetermined message on the display device 5.

Furthermore, the CPU 41 rewrites the polarizer deterioration information F in the flash memory 19 of the endoscope 2 to "1" (S18). Thus, the process of S18 constitutes an information writing section which writes the polarizer deterioration information F as predetermined information into the flash memory 19, which is a storage section provided for the endoscope 2, when the amount of change in the calculated color balance adjustment value is equal to or larger than the predetermined threshold (TH2).

At S16, when any one of the three absolute values of difference for the three RGB gain values is neither equal to nor larger than the predetermined threshold TH2 (S16: NO), the process ends.

When it is judged that the polarizers 18*a* and 18*b* have deteriorated as a result of the above process, the user requests a manufacturer to repair the endoscope 2, and the polarizers are replaced by the manufacturer of the endoscope 2.

When the polarizers 18*a* and 18*b* are replaced with new ones and fitted to the endoscope 2 by the manufacturer, each of the accumulated time period of use Ta and the polarizer deterioration information F in the flash memory 19 is rewritten to "0". Furthermore, the white balance process is performed in the factory, and a new reference color balance adjustment value Rg is written.

Note that, though the polarizer deterioration information F is flag information and is any of values "0" and "1" in the above example, the polarizer deterioration information F may be a counter value. For example, at S18 in FIG. 6, the count value is incremented at the time of writing a flag.

In that case, the value of the polarizer deterioration information F (the count value) indicates the number of times of outputting the message for repairing the endoscope at S7.

In the process in FIG. 6, when the accumulated time period of use Ta of the endoscope 2 exceeds the predetermined time period TH1, the process from S13 to S18 is executed each time the endoscope 2 is used unless the endoscope 2 is repaired and the accumulated time period of use Ta is rewritten to "0". Therefore, replacement of the polarizers 18*a* and 18*b* is prompted, and early repair is performed. Thereby, it does not happen that the user observes an endoscopic image changed due to deterioration of the polarizers.

As described above, according to the present embodiment, it is possible to realize an endoscope apparatus capable of detecting deterioration of polarizers provided for an endoscope, and, as a result, it is possible to prevent examination by an endoscopic image obtained by deteriorated polarizers, which is different from an endoscopic image in an optimal state, from being conducted.

Note that, though the gain value of each of RGB color signals is given as the color balance adjustment value in the above example, an output value for an amount of light of a light-emitting device of each of RGB colors (colors other than RGB are also possible) of an LED light source or the like may be used as the color balance adjustment value.

Furthermore, in the case where the LED light source is such that a device emitting each of RGB lights is configured with multiple light-emitting devices, and an amount of light can be adjusted according to the number of driven light-emitting devices, the color balance adjustment value may be the number of driven light-emitting devices of each color.

Second Embodiment

In the first embodiment, deterioration of the polarizers is detected by using the color balance adjustment value obtained in the white balance adjustment process. In a second embodiment, deterioration of the polarizers is detected by using a light adjustment value obtained in the white balance adjustment process.

Figure 8:
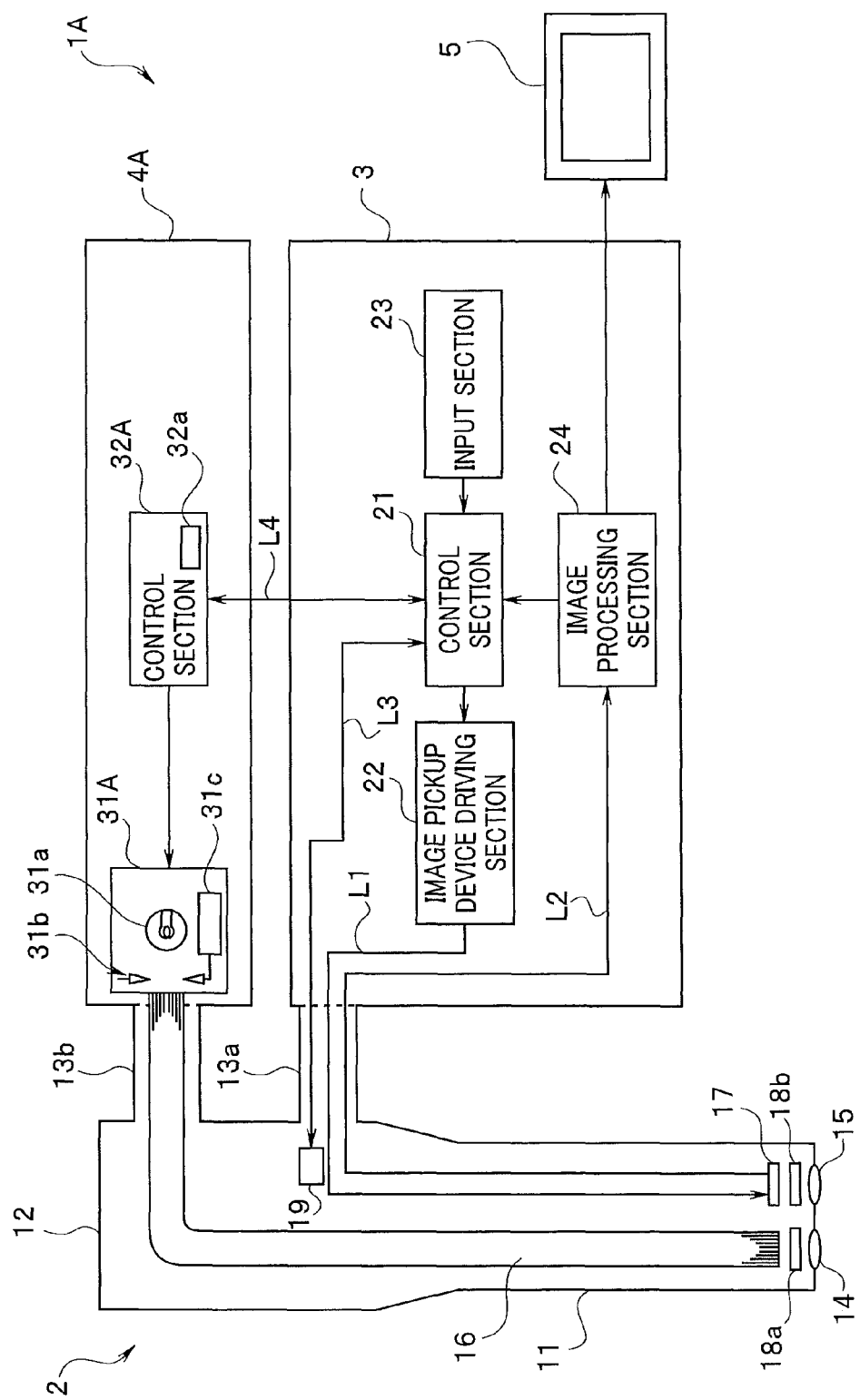
FIG. 8 is a configuration diagram showing a schematic configuration of an endoscope apparatus 1A according to a second embodiment of the present invention.

FIG. 8 is a configuration diagram showing a schematic configuration of an endoscope apparatus 1A according to the second embodiment of the present invention. Note that, in the second embodiment described below, same reference numerals will be used for same components as those of the endoscope apparatus 1 of the first embodiment, and description of the components will be omitted.

A light source apparatus 4A of the endoscope apparatus 1A includes a light source 31A and a control section 32A. The light source 31A includes a lamp 31*a* to be a light source, a diaphragm 31*b* for adjusting an amount of light which is emitted from the lamp 31*a* and enters the light guide 16, and a diaphragm driving section 31*c* which drives the diaphragm 31*b* to adjust a size of an opening of the diaphragm 31*b*. The control section 32A controls the diaphragm driving section 31*c* to adjust the diaphragm 31*b* so that an appropriate light adjustment state can be obtained.

The control section 32A includes a storage section 32*a* which stores an accumulated lamp lighting-up time period At of the lamp 31*a*. The control section 32A includes a CPU or a control circuit not shown, and accumulates and counts a time period during which the lamp 31*a* lights up after being fitted to the light source apparatus 4A for the first time and lit up first, and stores the time period into the storage section 32*a* as the accumulated lamp lighting-up time period At. The control section 32A updates the accumulated lamp lighting-up time period At of the storage section 32*a* by performing counting at predetermined time intervals when the lamp 31*a* lights up.

When the lamp 31*a* of the light source apparatus 4A is replaced with a new one, the accumulated lamp lighting-up time period At is initialized to "0 (zero)".

A hardware configuration of the control section 21 of the body device 3 is the same as the configuration shown in FIG. 2.

Figure 9:
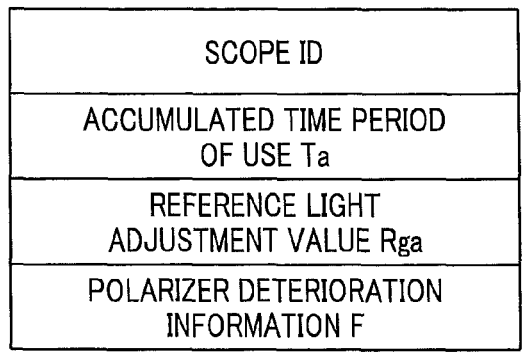
FIG. 9 is a diagram showing an example of information stored in a flash memory 19 of an endoscope 2 according to the second embodiment of the present invention.

FIG. 9 is a diagram showing an example of information stored in the flash memory 19 of the endoscope 2 of the present embodiment. The flash memory 19 includes a storage area for storing a scope ID, which is an identification code of the endoscope, the accumulated time period of use of endoscope Ta, a reference light adjustment value Rga and the polarizer deterioration information F. The reference light adjustment value Rga is reference information to be a criterion for judging deterioration of the polarizers 18a and 18b to be described later. Here, the reference light adjustment value Rga is a diaphragm initial value of the light source apparatus 4A at the time when the endoscope 2 is connected to the light source apparatus 4 first and the white balance process is performed. That is, the flash memory 19, which is a storage section, stores a reference value of the light adjustment value of the light source apparatus 4A connected to the endoscope 2.

Figure 10:
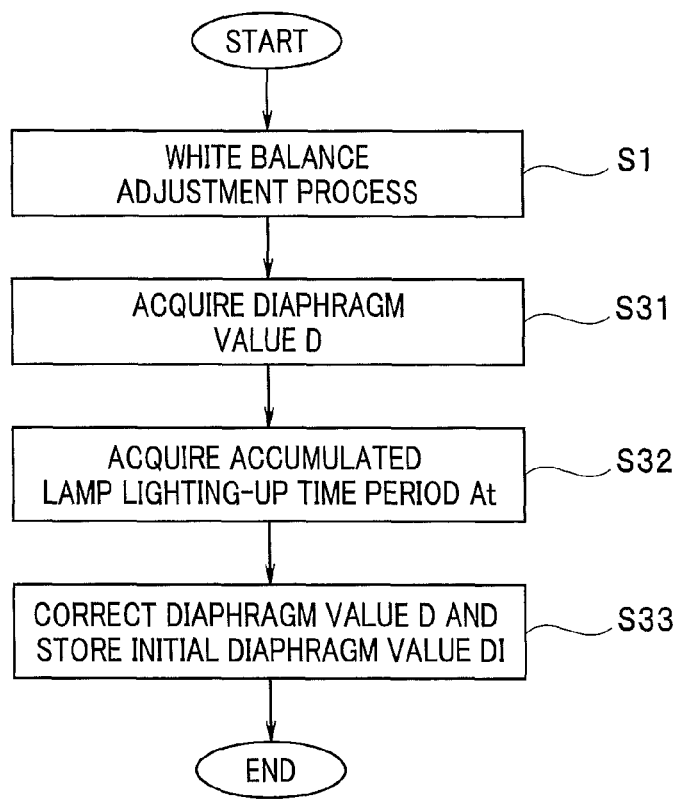
FIG. 10 is a flowchart showing an example of a flow of a procedure for setting a reference light adjustment value Rga according to the second embodiment of the present invention.

FIG. 10 illustrates a procedure for setting the reference light adjustment value Rga at the time when the endoscope 2 is connected to the light source apparatus 4A first. FIG. 10 is a flowchart showing an example of a flow of a procedure for setting the reference light adjustment value Rga.

As shown in FIG. 10, when the endoscope 2 is connected to the light source apparatus 4A first, the CPU 41 executes the white balance adjustment process (S1). The endoscope 2 is connected to the light source apparatus 4A used in combination with the endoscope 2, and the white balance adjustment process is executed.

In the white balance adjustment process, a white image is picked up, and gain adjustment is performed for each of RGB color signals so that the strengths of the three RGB color signals become the same. A diaphragm value D of the diaphragm 31b of the light source apparatus 4A at the time when the white balance adjustment is performed is acquired (S31).

Next, the CPU 41 acquires information about the accumulated lamp lighting-up time period At of the lamp 31a stored in the storage section 32a, from the control section 32A of the light source apparatus 4A (S32).

Then, the CPU 41 corrects the diaphragm value D acquired at S31 on the basis of the acquired information about the accumulated lamp lighting-up time period At of the lamp 31a and stores it into the flash memory 19 as an initial diaphragm value DI (S33).

Here, correction of the acquired diaphragm value D will be described.

Figure 11:
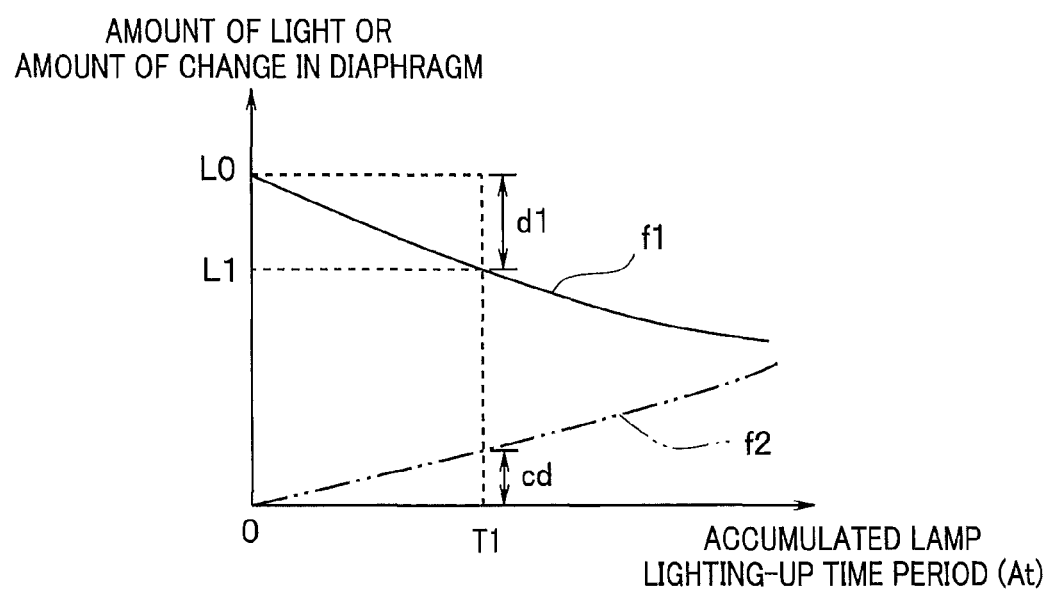
FIG. 11 is a schematic graph showing a relationship between an accumulated lamp lighting-up time period At of a lamp 31a, and an amount of light and an amount of diaphragm correction according to the second embodiment.

FIG. 11 is a schematic graph showing a relationship between the accumulated lighting-up time period of lamp At of the lamp 31a, and an amount of light and a diaphragm correction value. As the accumulated lamp lighting-up time period At is longer, the amount of light of the lamp 31a decreases.

As shown in FIG. 11, in the case of the light source apparatus 4A equipped with a new lamp 31a, the accumulated lamp lighting-up time period At is "0 (zero)", and, therefore, the amount of light does not decrease. Therefore, when the accumulated lamp lighting-up time period At is "0", the diaphragm value D acquired at S31 remains the diaphragm initial value DI, and the diaphragm value D is stored into the flash memory 19 as the reference light adjustment value Rga.

However, there may be a case where the accumulated lamp lighting-up time period At of the lamp 31a of the light source apparatus 4A is not "0" when the endoscope 2 is connected to the light source apparatus 4A first. When the accumulated lamp lighting-up time period At is T1, which is not "0", after the light source apparatus 4A is already used, the amount of light of the lamp 31a decreases. In FIG. 11, the amount of light at the time when the accumulated lamp lighting-up time period At is "0" is L0, and the amount of light at the time when the accumulated lamp lighting-up time period At is T1 decreases to L1.

As indicated by a solid line in FIG. 11, the amount of light changes such that it decreases with the accumulated lamp lighting-up time period At. The change is already known in advance by specifications of the lamp or experiments and can be expressed by a predetermined function f1.

As indicated by a two-dot chain line in FIG. 11, change in the diaphragm value D according to change in the amount of light of the lamp 31a during automatic light adjustment or during manual light adjustment is already known in advance and can be expressed by a different predetermined function f2.

That is, an amount of change d1 in the amount of light according to the accumulated lamp lighting-up time period At can be calculated from the predetermined function f1 of the accumulated lamp lighting-up time period At for an amount of light D0 at the time when the accumulated lamp lighting-up time period At is "0". Furthermore, an amount of change in the diaphragm value of the diaphragm 31b according to the amount of change in the amount of light or the accumulated lamp lighting-up time period At can be determined in advance.

Therefore, if the accumulated lamp lighting-up time period At of the lamp 31a of the light source apparatus 4A is not "0" when the endoscope 2 is connected to the light source apparatus 4A first, the CPU 41 calculates an amount of change cd in the diaphragm value from the accumulated lamp lighting-up time period At using the predetermined function f2 indicated by the two-dot chain line in FIG. 11, determines the initial diaphragm value DI from the calculated amount of change cd in the diaphragm value and the diaphragm value D acquired at S31, and stores the initial diaphragm value DI into a storage area for the reference light adjustment value Rga of the flash memory 19.

Thus, the initial diaphragm value DI, which is a reference value, is a value obtained by correcting the light adjustment value at the time when white balance adjustment is performed for an endoscopic image, on the basis of the accumulated lamp lighting-up time period At of the light source apparatus 4A connected to the endoscope 2. That is, the initial diaphragm value DI stored as the reference light adjustment value Rga is a diaphragm value at the time when the accumulated time period of use At estimated from the accumulated lamp lighting-up time period At is "0".

After that, the reference light adjustment value Rga is not rewritten until the endoscope 2 is repaired and the white balance process is performed in the factory again.

In the way described above, the initial diaphragm value DI is stored into the flash memory 19 of the endoscope 2. When the endoscope 2 is used for examination or the like, the polarizers 18a and 18b deteriorate with elapse of a time period.

Figure 12:
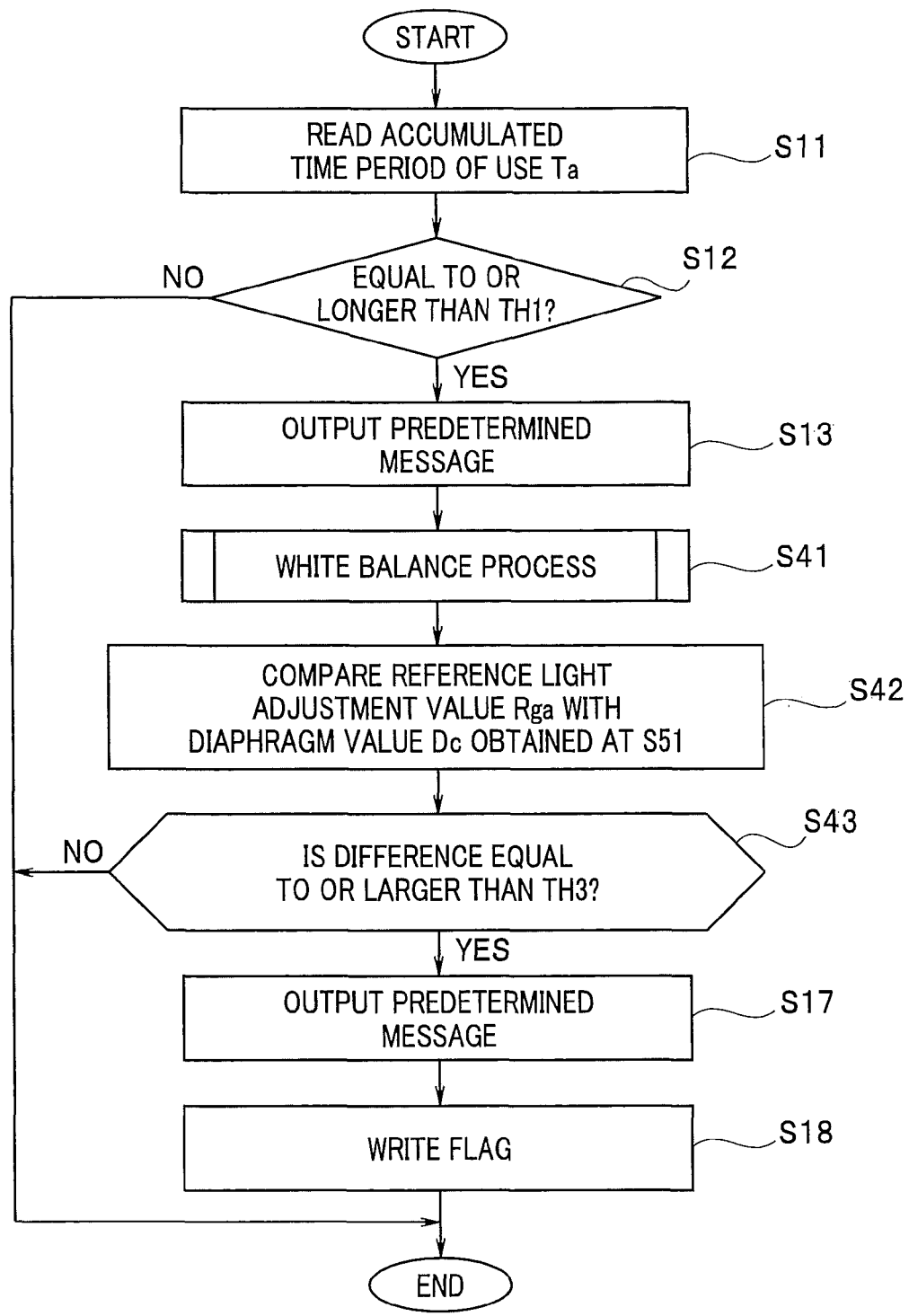
FIG. 12 is a flowchart showing an example of a flow of a process for detecting deterioration of the polarizers of the endoscope 2 according to the second embodiment of the present invention.

FIG. 12 is a flowchart showing an example of a flow of a process for detecting deterioration of the polarizers of the endoscope 2. In FIG. 12, same processes as those in FIG. 6 are given same reference numerals, and description thereof will be omitted. The process in FIG. 12 is also performed by the CPU 41 of the control section 21 reading a program for the process in FIG. 12 from the ROM 42 and executing the program.

First, the CPU 41 reads the accumulated time period of use Ta in the flash memory 19 of the endoscope 2 (S11) and judges whether or not the accumulated time period of use Ta is equal to or longer than a predetermined time period TH1 (S12).

When the accumulated time period of use Ta which has been read is equal to or longer than the predetermined time period TH1 (S12: YES), the CPU 41 outputs a predetermined message to the display device 5 (S13), and a white balance process is performed by the user in response to the message (S41).

Figure 13:
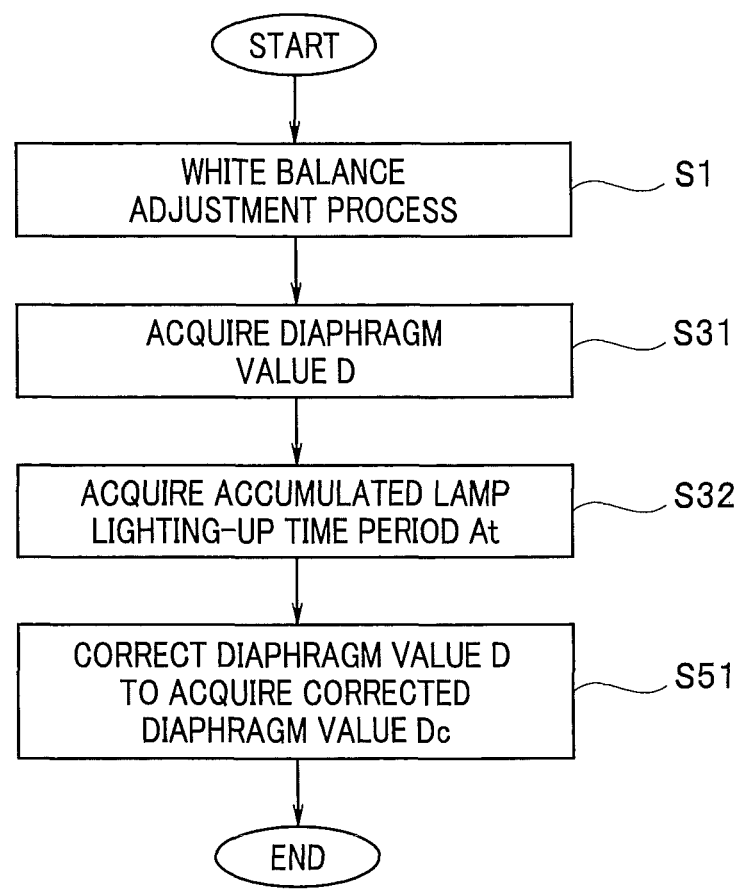
FIG. 13 is a flowchart showing an example of a flow of a white balance process (S41) in FIG. 12.

The white balance process is a process similar to the above-described process shown in FIG. 10. FIG. 13 is a flowchart showing an example of a flow of the white balance process (S41) in FIG. 12. The CPU 41 executes the white balance adjustment process (S1), and adjustment of a gain for each of RGB color signals is performed in the white balance adjustment process. The diaphragm value D of the diaphragm 31b of the light source apparatus 4 at the time when the white balance adjustment is performed is acquired (S31).

Next, the CPU 41 acquires information about the accumulated lamp lighting-up time period At of the lamp 31a stored in the storage section 32a from the control section 32A of the light source apparatus 4A (S32) and, as described in FIG. 11, corrects the diaphragm value D acquired at S31 on the basis of the acquired information about the accumulated lamp lighting-up time period At of the lamp 31a to acquire a corrected diaphragm value Dc (S51).

The correction of the diaphragm value D at S51 is performed by subtracting a value of increase in the diaphragm value according to decrease in the amount of light of the lamp 31a, from the diaphragm value D acquired at S31. For example, in FIG. 11, when the accumulated lamp lighting-up time period At is T1, the amount of change cd is subtracted from the diaphragm value D acquired at S31, and a corrected diaphragm value Dc is (D−cd). That is, the diaphragm value Dc, which is a light adjustment value of the light source apparatus 4A after elapse of the predetermined time period (TH1), is a value corrected on the basis of the accumulated lamp lighting-up time period At of the light source apparatus 4A connected to the endoscope 2.

Returning to FIG. 12, the CPU 41 compares the initial diaphragm value DI, which is the reference light adjustment value Rga, and the diaphragm value Dc obtained at S51 (S42). That is, comparison between the diaphragm value Dc corrected with the accumulated lamp lighting-up time period At, which has been acquired at S51, and the initial diaphragm value DI included in the reference light adjustment value Rga is performed. More specifically, difference between the corrected diaphragm value Dc obtained at S51 and the diaphragm value DI included in the reference light adjustment value Rga is determined, and the difference is calculated. Thus, the process of S42 constitutes the amount-of-change calculating section which calculates an amount of change in the light adjustment value of the light source apparatus 4A from the reference light adjustment value Rga, which is a reference value, and the diaphragm value, which is a light adjustment value of the light source apparatus 4A after elapse of the predetermined time period (TH1).

The CPU 41 judges whether or not an absolute value of difference between the diaphragm value Dc and the initial diaphragm value DI included in the reference light adjustment value Rga is equal to or larger than a predetermined threshold TH3 (S43). That is, the process of S43 constitutes the judgment section which judges whether or not the amount of change in the calculated light adjustment value is equal to or larger than the predetermined threshold (TH3).

If the absolute value of the difference between the diaphragm value Dc and the initial diaphragm value DI is equal to or larger than the predetermined threshold TH3 (S43: YES), the CPU 41 outputs a predetermined message to the display device 5 (S17). Thus, the process of S17 constitutes the output section which performs a predetermined output when the amount of change in the light adjustment value is equal to or larger than the predetermined threshold (TH3).

Especially, the predetermined output at S17 is a message output for displaying a predetermined message on the display device 5.

Then, the CPU 41 rewrites the polarizer deterioration information F in the flash memory 19 of the endoscope 2 to "1" (S18). Thus, the process of S18 constitutes the information writing section which writes predetermined information into the flash memory 19, which is a storage section provided for the endoscope 2, when the amount of change in a calculated light adjustment value is equal to or larger than the predetermined threshold (TH3).

When the absolute value of the difference between the diaphragm value Dc and the initial diaphragm value DI is neither equal to nor larger than the predetermined threshold TH3 at S43 (S43: NO), the process ends.

For example, it is assumed that the initial diaphragm value DI is "+1" when a diaphragm adjustment range is from −8 to +8. The polarizers 18a and 18b deteriorate with elapse of a time period, and the amount of light of the lamp 31a also decreases. The diaphragm value of the diaphragm 31b of the light source apparatus 4 at the time when white balance adjustment is performed when the accumulated lamp lighting-up time period At is T1 includes influence by deterioration of the polarizers 18a and 18b and influence by deterioration of the lamp 31a of the light source 31A.

Therefore, at S51, the diaphragm value D acquired at S31 is corrected with the amount of change cd in the diaphragm value according to decrease in the amount of light of the lamp 31a due to the accumulated lamp lighting-up time period At to acquire a corrected diaphragm value Dc. If the diaphragm value acquired at S31 is "+3" and the amount of change cd in the diaphragm value caused by decrease in the amount of light in the lamp 31a is "+1", the corrected diaphragm value Dc is "2=(3−1)". That is, the corrected diaphragm value Dc is a diaphragm value on the assumption that there is not decrease in the amount of light of the light source 31A with elapse of a time period and is a diaphragm value changed due to deterioration of the polarizers 18a and 18b.

The corrected diaphragm value Dc is compared with the predetermined threshold TH3, and judgment about whether the polarizers 18a and 18b have deteriorated or not is performed.

When it is judged that the polarizers 18a and 18b have deteriorated as a result of the above process, the user requests a manufacturer to repair the endoscope 2, and the polarizers are replaced by the manufacturer of the endoscope 2.

When the polarizers 18a and 18b are replaced with new ones and fitted to the endoscope 2 by the manufacturer, each of the accumulated time period of use Ta and the polarizer deterioration information F in the flash memory 19 is rewritten to "0". Furthermore, the white balance process is performed in the factory, and a new reference light adjustment value Rga is written.

Note that, though the light adjustment value is the diaphragm value of the light source apparatus 4A in the example described above, the light adjustment value may be a drive output value of the lamp 31a.

Furthermore, note that, in the present embodiment also, the polarizer deterioration information F may be a counter value.

As described above, according to the present embodiment, it is possible to realize an endoscope apparatus capable of detecting deterioration of polarizers provided for an endoscope, and, as a result, it is possible to prevent examination by an endoscopic image obtained by deteriorated polarizers, which is different from an endoscopic image in an optimal state, from being conducted.

Next, modifications related to the endoscope apparatuses of the two embodiments described above will be described.

Modification 1

There are one reference color balance adjustment value Rg and one reference light adjustment value Rga as reference information for deterioration judgment in the two embodiments described above. However, the endoscope 2 is not necessarily connected to only one determined light source apparatus 4 or 4A, and there may be a case where the endoscope 2 is connected to multiple light source apparatuses and used.

In such a case, the reference color balance adjustment value Rg and the reference light adjustment value Rga stored in the flash memory 19 may be stored in each light source apparatus. That is, the flash memory 19, which is a storage section, stores the reference color balance adjustment value Rg and the reference light adjustment value Rga as reference values for each of multiple light source apparatuses to be connected to the endoscope 2.

FIG. 14 is a diagram showing an example of information stored in the flash memory 19 of the endoscope 2 according to the present modification 1. FIG. 14 shows an example of the flash memory 19 of the endoscope 2 of the first embodiment. In FIG. 14, the scope ID, which is the identification code of the endoscope, the accumulated time period of use Ta and the polarizer deterioration information F are the same as FIG. 4.

However, the reference color balance adjustment value Rg is stored for each light source apparatus. In FIG. 14, a reference color balance adjustment value Rg1 for a light source apparatus 4-1, a reference color balance adjustment value Rg2 for a light source apparatus 4-2 and a reference color balance adjustment value Rg3 for a light source apparatus 4-3 are stored in the flash memory 19.

When the light source apparatus 4 is connected, the CPU 41 checks whether a reference color balance adjustment value Rg for the connected light source apparatus is stored or not, from the scope ID of the light source apparatus. If the reference color balance adjustment value Rg for the connected light source apparatus is already stored in the flash memory 19, the reference color balance adjustment value Rg can be used as it is.

If the reference color balance adjustment value Rg for the connected light source apparatus is not stored in the flash memory 19, a procedure for setting the reference color balance adjustment value Rg by the white balance process shown in FIG. 5. is executed, and the reference color balance adjustment value Rg for the light source apparatus is stored into the flash memory 19.

As described above, in the case of a new combination of an endoscope 2 and a light source apparatus 4, a reference color balance adjustment value Rg corresponding to the light source apparatus 4 is newly added to and set in the flash memory 19.

The same goes for the second embodiment. In the case of a new combination of an endoscope 2 and a light source apparatus 4A, a reference light adjustment value Rga corresponding to the light source apparatus 4A is newly added to and set in the flash memory 19.

Note that, in the case of the second embodiment, since the functions f1 and f2 described in FIG. 11 also differ for each light source apparatus, correction corresponding to the functions is performed in the process for setting the reference light adjustment value Rga and the process for detecting deterioration of the polarizers 18a and 18b.

Modification 2

In the second embodiment, an acquired light adjustment value is corrected with the use of decrease in the amount of light caused by deterioration of the lamp 31a of the light source apparatus 4A. In the first embodiment also, the color balance adjustment value may be corrected in consideration of deterioration of the light source 31 of the light source apparatus 4.

That is, in the first embodiment, if the color balance adjustment value changes according to change in the amount of light caused by elapse of a time period for each LED, an amount of correction of the color balance value on the basis of a function F of decrease in the amount of light caused by elapse of a time period for each LED is determined in advance.

Then, at the time of storing the gain value of each color signal as the color balance adjustment value in FIG. 5, the gain value is corrected from the accumulated lighting-up time period of the light source apparatus 4 is corrected on the basis of the function F and stored into the flash memory 19 as a color balance adjustment value.

Furthermore, when the gain value of each color signal as a color balance adjustment value is acquired at S21 in FIG. 7, the gain value is corrected with the use of the amount of change in the color balance adjustment value caused by elapse of a predetermined time period determined on the basis of the function F.

As described above, the color balance adjustment value of the endoscope 2 after elapse of a predetermined time period is a value obtained by correcting the color balance adjustment value at the time when white balance adjustment is performed for an endoscopic image, on the basis of an accumulated lighting-up time period of the light source apparatus 4 connected to the endoscope 2. Therefore, in the first embodiment also, deterioration of the polarizers may be detected by correcting the color balance adjustment value using the amount of change in the color balance adjustment value caused by elapse of a time period for each LED.

As described above, according to each embodiment and each modification described above, it is possible to realize an endoscope apparatus capable of detecting deterioration of polarizers provided for an endoscope, and, as a result, it is possible to prevent examination by an endoscopic image obtained by deteriorated polarizers, which is different from an endoscopic image in an optimal state, from being conducted.

The present invention is not limited to the embodiments described above, and various changes, alterations and the like are possible within a range not departing from the spirit of the present invention.

What is claimed is:
1. An endoscope apparatus comprising:
a storage section that stores a reference value, which is a color balance adjustment value at a time of adjusting an endoscopic image obtained from an endoscope to be of predetermined color balance, in the endoscope that picks up an object through a polarizer;
an amount-of-change calculating section that calculates, from the reference value stored in the storage section and the color balance adjustment value at the time of adjusting the endoscopic image after elapse of a predeter- mined time period to be of the predetermined color balance, an amount of change in the color balance adjustment value;

a judgment section that judges whether or not the amount of change calculated at the amount-of-change calculating section is equal to or larger than a predetermined threshold; and an output section that performs a predetermined output when it is judged at the judgment section that the amount of change is equal to or larger than the predetermined threshold.

2. The endoscope apparatus according to claim 1, wherein the color balance adjustment value is a gain value of each color or an output value of or a number of times of driving a light-emitting device of each color at the time of performing color balance adjustment for the endoscopic image.

3. The endoscope apparatus according to claim 1, wherein the color balance adjustment value of the endoscope after elapse of the predetermined time period is a value obtained by correcting the color balance adjustment value at the time of performing color balance adjustment for the endoscopic image on the basis of an accumulated lighting-up time period of a light source apparatus connected to the endoscope.

4. The endoscope apparatus according to claim 1, wherein, when an accumulated time period of use of the endoscope becomes equal to or longer than a predetermined period, the calculation of the amount of change by the amount-of-change calculating section and the judgment by the judgment section about whether or not the amount of change is equal to or larger than the predetermined threshold are performed.

5. The endoscope apparatus according to claim 1, wherein the output section performs the predetermined output when at least one of color signals of respective colors of the endoscopic image is equal to or larger than the predetermined threshold.

6. The endoscope apparatus according to claim 1, wherein the predetermined output by the output section is a message output for displaying a predetermined message on a display device.

7. A method for detecting deterioration of a polarizer of an endoscope, the method comprising:

storing a reference value, which is a color balance adjustment value at a time of adjusting an endoscopic image obtained from an endoscope to be of predetermined color balance, in the endoscope that picks up an object through the polarizer, into a storage section;

calculating, from the reference value stored in the storage section and the color balance adjustment value at the time of adjusting the endoscopic image after elapse of a predetermined time period to be of the predetermined color balance, an amount of change in the color balance adjustment value;

judging whether or not the calculated amount of change is equal to or larger than a predetermined threshold; and performing a predetermined output when it is judged that the amount of change is equal to or larger than the predetermined threshold.

8. An endoscope apparatus comprising:

a storage section that stores a reference value of a light adjustment value of a light source apparatus connected to an endoscope that picks up an object through a polarizer;

an amount-of-change calculating section that calculates, from the reference value stored in the storage section and the light adjustment value of the light source apparatus after elapse of a predetermined time period, an amount of change in the light adjustment value of the light source apparatus;

a judgment section that judges whether or not the amount of change calculated at the amount-of-change calculating section is equal to or larger than a predetermined threshold; and an output section that performs a predetermined output when it is judged at the judgment section that the amount of change is equal to or larger than the predetermined threshold.

9. The endoscope apparatus according to claim 8, wherein the light adjustment value of the light source apparatus is the light adjustment value of the light source apparatus at the time of color balance adjustment for an endoscopic image of the endoscope.

10. The endoscope apparatus according to claim 9, wherein the light adjustment value is a diaphragm value of the light source apparatus or a drive output value of the light source apparatus.

11. The endoscope apparatus according to claim 8, wherein, when an accumulated time period of use of the endoscope becomes equal to or longer than a predetermined period, the calculation of the amount of change by the amount-of-change calculating section and the judgment by the judgment section about whether or not the amount of change is equal to or larger than the predetermined threshold are performed.

12. The endoscope apparatus according to claim 8, wherein the reference value is a value obtained by correcting the light adjustment value at the time of performing color balance adjustment of the endoscopic image on the basis of an accumulated lighting-up time period of the light source apparatus connected to the endoscope.

13. The endoscope apparatus according to claim 8, wherein the light adjustment value of the light source apparatus after elapse of the predetermined time period is a value corrected on the basis of an accumulated lighting-up time period of the light source apparatus connected to the endoscope.

14. The endoscope apparatus according to claim 8, wherein the predetermined output by the output section is a message output for displaying a predetermined message on a display device.

15. A method for detecting deterioration of a polarizer of an endoscope, the method comprising:

storing a reference value of a light adjustment value of a light source apparatus connected to an endoscope that picks up an object through the polarizer, into a storage section;

calculating, from the reference value stored in the storage section and the light adjustment value of the light source apparatus after elapse of a predetermined time period, an amount of change in the light adjustment value of the light source apparatus;

judging whether or not the calculated amount of change is equal to or larger than a predetermined threshold; and performing a predetermined output when it is judged that the amount of change is equal to or larger than the predetermined threshold.

* * * * *

UNITED STATES PATENT AND TRADEMARK OFFICE
CERTIFICATE OF CORRECTION

PATENT NO. : 8,937,652 B2  Page 1 of 1
APPLICATION NO. : 14/210763
DATED : January 20, 2015
INVENTOR(S) : Daiki Ariyoshi et al.

It is certified that error appears in the above-identified patent and that said Letters Patent is hereby corrected as shown below:

On the Title Page

It Should Read:

(54)    ENDOSCOPE APPARATUS AND METHOD FOR DETECTING DETERIORATION OF POLARIZER OF ENDOSCOPE

Signed and Sealed this
Fourteenth Day of July, 2015

Michelle K. Lee
*Director of the United States Patent and Trademark Office*